(12) United States Patent
Janice

(10) Patent No.: US 8,894,689 B2
(45) Date of Patent: Nov. 25, 2014

(54) STABILIZATION ROD ASSEMBLY FOR SPINE FIXATION AND PROCESS OF MAKING SAME

(75) Inventor: David Janice, Austin, TX (US)

(73) Assignee: Omni Acquisitions, Inc., Marietta, GA (US)

( * ) Notice: Subject to any disclaimer, the term of this patent is extended or adjusted under 35 U.S.C. 154(b) by 271 days.

(21) Appl. No.: 13/451,648

(22) Filed: Apr. 20, 2012

(65) Prior Publication Data

US 2013/0282061 A1 Oct. 24, 2013

(51) Int. Cl.
*A61B 17/70* (2006.01)

(52) U.S. Cl.
USPC .................................. 606/257; 606/259

(58) Field of Classification Search
USPC ............... 606/53, 60, 246–279, 300–320, 606/325–328
See application file for complete search history.

(56) References Cited

U.S. PATENT DOCUMENTS

| | | | |
|---|---|---|---|
| 4,369,769 A | 1/1983 | Edwards | |
| 4,998,936 A | 3/1991 | Mehdian | |
| 5,084,049 A | 1/1992 | Asher | |
| 5,217,461 A | 6/1993 | Asher | |
| 6,309,389 B1 * | 10/2001 | Baccelli | 606/264 |
| 7,326,210 B2 | 2/2008 | Jahng | |
| 7,618,442 B2 * | 11/2009 | Spitler et al. | 606/266 |
| 7,875,059 B2 | 1/2011 | Patterson | |
| 7,927,356 B2 * | 4/2011 | Lim | 606/257 |
| 7,951,170 B2 | 5/2011 | Jackson | |
| 8,221,467 B2 * | 7/2012 | Butler et al. | 606/257 |
| 2007/0049937 A1 | 3/2007 | Matthis et al. | |
| 2007/0191842 A1 * | 8/2007 | Molz et al. | 606/61 |
| 2007/0270821 A1 * | 11/2007 | Trieu et al. | 606/61 |
| 2008/0015585 A1 | 1/2008 | Berg | |
| 2008/0255617 A1 * | 10/2008 | Cho et al. | 606/246 |
| 2009/0287260 A1 * | 11/2009 | Zehnder | 606/305 |
| 2010/0268281 A1 * | 10/2010 | Abdou | 606/279 |
| 2010/0318130 A1 | 12/2010 | Parlato | |
| 2011/0251648 A1 * | 10/2011 | Fiechter et al. | 606/286 |

* cited by examiner

*Primary Examiner* — Pedro Philogene
*Assistant Examiner* — Lynnsy Summitt
(74) *Attorney, Agent, or Firm* — David O. Simmons

(57) ABSTRACT

A spine stabilization rod assembly comprises a rod and a sleeve member. The rod has a substantially round cross-sectional profile, a one-piece construction, and a substantially straight longitudinal axis. The rod has a reduced diameter segment between two opposing end segments thereof such that a shoulder is defined between the reduced diameter segment and each one of the end segments. The sleeve member is positioned over the reduced diameter segment of the rod. The sleeve member and the rod are coupled to each other such that translation of the sleeve along the rod causes an end portion of the sleeve to engage a corresponding one of the shoulders for limiting such translation.

17 Claims, 2 Drawing Sheets

STABILIZATION ROD ASSEMBLY FOR SPINE FIXATION AND PROCESS OF MAKING SAME

FIELD OF THE DISCLOSURE

The disclosures made herein relate generally to spine fixation and, more particularly, to stabilization rods and stabilization rod assemblies used in combination with implements such as poly-axial pedicle screws.

BACKGROUND

Traditional spinal fixation, which is often referred to as rigid fixation, involves immobilizing spine segments (e.g., vertebrae) using a rigid spine stabilization rod that is connected between. Generally speaking, such a rigid spine stabilization rod is solid and has a uniform cross-section shape. One known drawback of such rigid fixation is an increase in motion of adjacent spine segments. Undesirably, this increased motion can impart significant unintended strain on to these adjacent spine segments and lead to further injury and pain. Therefore, spine stabilization rods and rod assemblies that offer a controlled amount of flexibility are beneficial, desirable and useful in spine fixation applications.

SUMMARY OF THE DISCLOSURE

Embodiments of the present invention relate to a flexible spine stabilization rod assembly useful in spine fixations procedures. More specifically, embodiments of the present invention include a spine stabilization rod assembly that includes a rod having a central segment that provides for a preferential flexure location. For example, the central segment can have a reduced outside diameter relative to an outside diameter of portions of the rod that are configured for being engaged with an associated device such as a poly-axial pedicle screw assembly. A sleeve member of the rod assembly is coupled to the rod over its reduced diameter portion for limiting unrestricted being of the reduced diameter portion. In this manner, embodiments of the present invention advantageously and beneficially enhance flexing of a spine stabilization rod assembly for allowing a desired amount of movement of attached segments of the spine thereby limiting undesirable strain on to these adjacent spine segments. By limiting this undesirable strain on to these adjacent segments of the spine, the potential for further injury and pain in these adjacent spine segments.

In one embodiment of the present invention, a spine stabilization rod assembly comprises a rod and a sleeve member. The rod has a one-piece construction, and a substantially straight longitudinal axis. The rod has a reduced diameter segment between two opposing end segments thereof such that a shoulder is defined between the reduced diameter segment and each one of the end segments. The sleeve member is positioned over the reduced diameter segment of the rod. The sleeve member and the rod are coupled to each other such that translation of the sleeve along the rod causes an end portion of the sleeve to engage a corresponding one of the shoulders for limiting such translation.

In another embodiment of the present invention, a spine stabilization rod assembly comprises a one-piece rod and a sleeve member. The one-piece rod has opposing end segments and a central segment extending between the opposing end segments. The one-piece rod is substantially straight. A transition from the central segment to each one of the end segments defines a respective shoulder. The sleeve member is coupled to the central segment of the one-piece rod. The central segment passes through a central passage of the sleeve member. End portions of the sleeve member are engaged with the central segment for limiting unrestricted displacement of the sleeve member along a length of the central segment.

In another embodiment of the present invention, a spine stabilization rod assembly comprises a rod and a plurality of sleeve members. The rod has a substantially round cross-sectional profile, a one-piece construction, and a substantially straight longitudinal axis. The rod has a plurality of reduced diameter segments each between two adjacent nominal diameter segments thereof such that a shoulder is provided between each one of the reduced diameter segments and each adjacent one of the nominal diameter segments. Each one of the plurality of sleeve members is positioned over a respective one of the reduced diameter segments of the rod. The sleeve members and the rod are coupled together such that translation of a particular one of the sleeve members along the rod causes an end portion of the sleeve member to engage an adjacent shoulder of a respective one of the reduced diameter segments thereby limiting such translation.

These and other objects, embodiments, advantages and/or distinctions of the present invention will become readily apparent upon further review of the following specification, associated drawings and appended claims.

DETAILED DESCRIPTION OF THE DRAWING FIGURES

Figure 1:
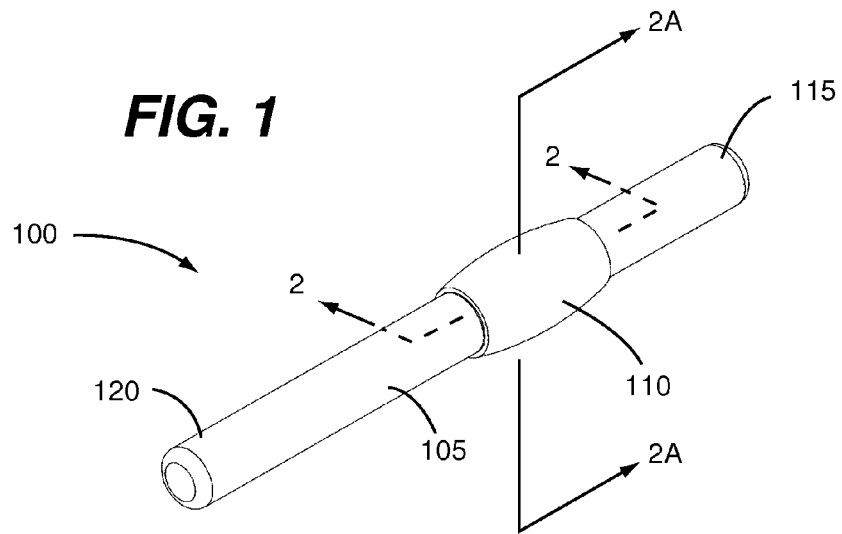
FIG. 1 is a perspective view showing a spine stabilization rod assembly configured in accordance with a first embodiment of the present invention.
Figure 2:
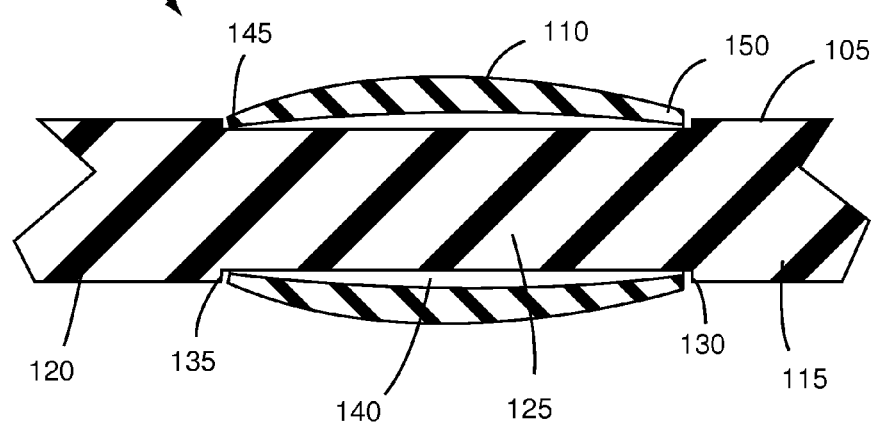
FIG. 2 is a cross sectional view taken along the line 2-2 in FIG. 1.
Figure 2A:
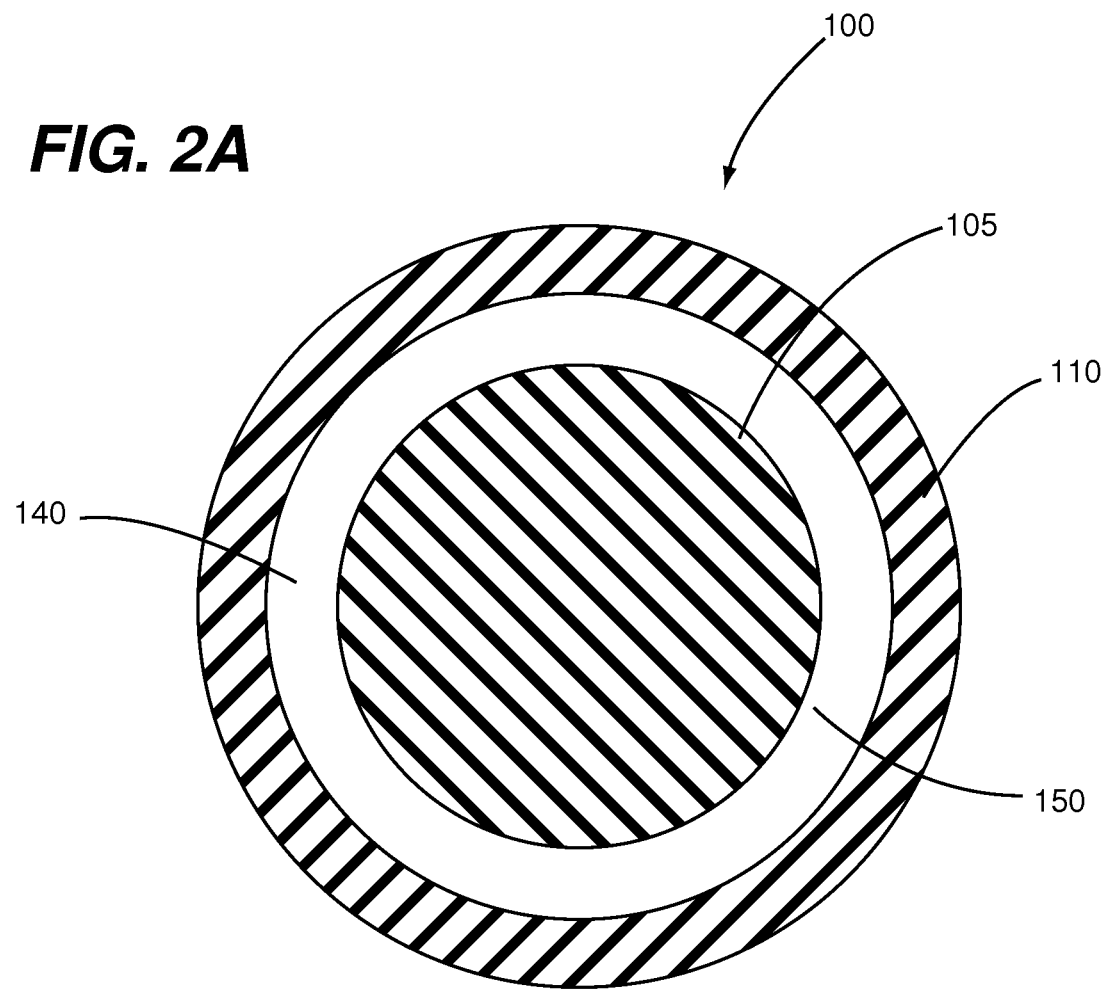
FIG. 2A is a cross-sectional view taken along the line 2A-2A in FIG. 1, wherein a view taken 180-degrees from the cross-sectional view taken along the line 2A-2A in FIG. 1 would be a mirror image of FIG. 2A.

FIGS. 1, 2 and 2A show a spine stabilization rod assembly 100 configured in accordance with a first embodiment of the present invention. The spine stabilization rod assembly 100 includes a rod 105 and a sleeve member 110. The rod 105 has a first end segment 115, a second end segment 120 (i.e., opposing end segments), and a central segment 125 extending between the first and second end segments 115, 120. A maximum outside diameter of the central segment 125 is less than a maximum outside diameter of each one of the end segments 115, 120 such that a transition from the central segment 125 to each one of the end segments includes a respective shoulder 130, 135. In this manner, the central segment 125 is a reduced diameter segment with regard to each one of the end segments 115, 120.

The sleeve member 110 is coupled to the central segment 125 of the rod 105. The central segment 125 passes through a central passage 140 of the sleeve member 110. Preferably, an overall length of the sleeve member 110 is less than a length of the central segment 125 such that a first end portion 145 and a second end portion 150 of the sleeve member 110 are engaged with the central segment 225 for limiting unrestricted displacement of the sleeve member 110 along a length of the central segment 125. In this regard, an entire portion of the sleeve member 110 is preferably positioned over the central segment 125 (i.e., the first end portion 145 and the second end portion 150 of the sleeve member 110 are located between the shoulders 130, 135 of the central segment 125 of the rod 105.

As shown, the tip portions of the rod 105 are generally flat with chamfered edges. However, in other embodiments, the tip portions can have other configurations. In one such embodiment, one or both of the tip portions can be hemispherically shaped or bullet shaped (e.g., a hemispherical tip with conical transition segment). In another such embodiment, one or both of the tip portions can include a coupling structure for enabling a tip portion of the rod 105 to be coupled to a rod placement apparatus in a manner that substantially limits relative movement of the rod 105 with respect to an attached portion of the rod placement apparatus.

It is disclosed herein that the end segments 115, 120 can both have a substantially round cross-sectional profile and can have substantially the same maximum outside diameter (i.e., as shown) or can have substantially different maximum outside diameters. It is also disclosed herein that the first end segment 115 can have a substantially round cross-sectional profile and the second end segment 120 can have a substantially non-round cross-sectional profile. Examples of non-round cross-sectional profiles include, but are not limited to, an oval cross-sectional profile, a rectangular cross-sectional profile, a T-shaped cross sectional profile, and a dovetail shaped cross sectional profile.

The rod is preferably of a one-piece, solid construction and is preferably but not necessarily substantially straight. Titanium is a preferred material for both the rod 105 and the sleeve member 110. However, the rod 105 and/or the sleeve member 110 can be made from another material such as, for example, stainless steel or a suitable polymeric material.

Presented now is a discussion on an embodiment of a process of making the spine stabilization rod assembly 100. The process starts with sliding the sleeve member 110 over the first end segment 115 of the rod 105 such that the rod 105 is within the central bore 140 of the sleeve member 110. Accordingly, in an as-manufactured configuration, a minimum inside diameter of the central passage 140 of the sleeve member 110 is equal to or slightly larger than a maximum outside diameter of the rod 105. Next, the sleeve member 110 is positioned such that an entire portion of the sleeve member 110 is positioned over the central segment 125. Thereafter, at least one of the end portions 145, 150 of the sleeve member 110 are deformed into contact with the central segment 125 of the rod 105 (i.e., the reduced diameter segment thereof). Rolling and or swagging are examples of techniques for deforming the end portions of the sleeve member 110.

Figure 3:
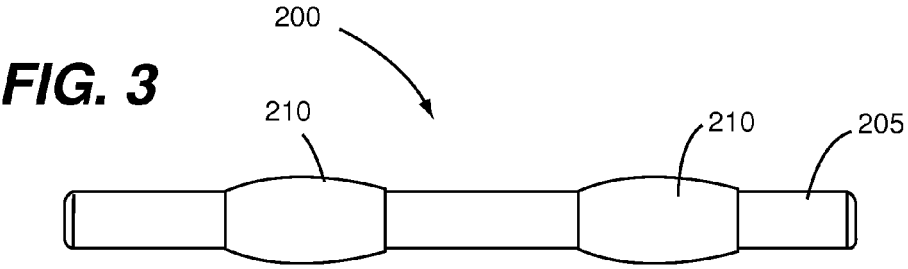
FIG. 3 is a perspective view showing a spine stabilization rod assembly configured in accordance with a second embodiment of the present invention.

Referring now to FIG. 3, a spine stabilization rod assembly 200 configured in accordance with a second embodiment of the present invention is shown. The spine stabilization rod assembly 200 includes a rod 205 and a plurality of sleeve members 210. The rod 205 is generally the same construction as the rod 105 discussed above, except with a plurality of reduced diameter segments each between two adjacent nominal diameter segments. In this regard, a shoulder is provided between a particular one of the reduced diameter segments and each adjacent nominal diameter segment. Each one of the plurality of sleeve members 210, which are generally of the same configuration as the sleeve member 110 discussed above in reference to FIGS. 1 and 2, is positioned over a respective one of the reduced diameter segments of the rod 205. The sleeve members 210 and the rod 205 are coupled together such that translation of a particular one of the sleeve members 210 along the rod 205 causes an end portion of the sleeve member 210 to engage an adjacent shoulder of a respective one of the reduced diameter segments thereby limiting such translation. Each one of the sleeve members 210 can be coupled to the rod 205 in the same manner as discussed above in reference to the process for making the spine stabilization rod assembly 100.

Advantageously, spine stabilization rod assemblies configured in accordance with embodiments of the present invention allow desirable and beneficial amounts of flexure of the rod at lower flexion/extension/rotation loads to that of traditional rods and rod assemblies (e.g., rigid rods/rod assemblies). This is advantageous in that it aids in reducing the potential further injury or pain at portions of the spine that are adjacent to the spine rod placement. Conversely, in the case of hyper-flexion or extension, the sleeve member of a spine stabilization rod assembly configured in accordance with an embodiment of the present invention provides rod stiffening functionality as it comes into contact with the central segment of the rod during flexing of the rod. Accordingly, by load sharing, the sleeve member in combination with the rod mitigates further bending of the rod under inadvertent loading by causing the rod assembly to become stiffer than its initial unloaded configuration (i.e., the reduced diameter portion not being in contact with the inner surface of the central bore of the sleeve member).

In the preceding detailed description, reference has been made to the accompanying drawings that form a part hereof, and in which are shown by way of illustration specific embodiments in which the present invention may be practiced. These embodiments, and certain variants thereof, have been described in sufficient detail to enable those skilled in the art to practice embodiments of the present invention. It is to be understood that other suitable embodiments may be utilized and that logical, mechanical, chemical and electrical changes may be made without departing from the spirit or scope of such inventive disclosures. To avoid unnecessary detail, the description omits certain information known to those skilled in the art. The preceding detailed description is, therefore, not intended to be limited to the specific forms set forth herein, but on the contrary, it is intended to cover such alternatives, modifications, and equivalents, as can be reasonably included within the spirit and scope of the appended claims.

What is claimed is:

1. A spine stabilization rod assembly, comprising:
a rod having a one-piece construction, and a substantially straight longitudinal axis, wherein the rod has a reduced diameter segment between two opposing end segments thereof such that a shoulder is defined between the reduced diameter segment and each one of the end segments; and
a sleeve member positioned over the reduced diameter segment of the rod, wherein the sleeve member is positioned over the reduced diameter segment of the rod by relative displacement of the rod through a central passage of the sleeve member, wherein only opposing end portions of the sleeve member are deformed such that translation of the sleeve along the rod causes an end portion of the sleeve to engage a corresponding one of the shoulders for limiting such translation and such that an entire portion of an inner surface of the central passage of the sleeve member between said deformed opposing end portions of the sleeve member is spaced away from an entire underlying portion of the reduced diameter segment of the rod after the opposing end portions thereof are deformed.

2. The spine stabilization rod assembly of claim 1 wherein:
a first one of the end segments has a maximum outside diameter less than a minimum inside diameter of the central passage of the sleeve member prior to the opposing end portions thereof being deformed; and;
an overall length of the sleeve member is less than an overall length of the reduced diameter segment.

3. The spine stabilization rod assembly of claim 2 wherein:
the first one of the end segments has a substantially round cross-sectional profile; and
a second one of said end segments has one of a substantially non-round cross-sectional profile and a substantially round cross-sectional profile having a maximum outside diameter that is substantially greater than a maximum outside diameter of the first end segment.

4. The spine stabilization rod assembly of claim 1 wherein:
the first one of the end segments has a substantially round cross-sectional profile; and
a second one of said end segments has one of a substantially non-round cross-sectional profile and a substantially round cross-sectional profile having a maximum outside diameter that is substantially greater than a maximum outside diameter of the first end segment.

5. The spine stabilization rod assembly of claim 1, made by the process comprising:
sliding the sleeve member onto the rod such that the rod is within the central passage of the sleeve member;
positioning the sleeve member over the reduced diameter segment; and
deforming only the opposing end portions of the sleeve member into contact with rod.

6. The spine stabilization rod assembly of claim 5 wherein an overall length of the sleeve member is less than an overall length of the reduced diameter segment.

7. The spine stabilization rod assembly of claim 1 wherein:
an overall length of the sleeve member is less than an overall length of the reduced diameter segment; and
an entire portion of the sleeve member is over the reduced diameter segment.

8. The spine stabilization rod assembly of claim 7 wherein only the opposing end portions of the sleeve member are deformed from an as-manufactured configuration thereof such that the deformed opposing end portions of the sleeve member are each engaged with the reduced diameter segment of the rod.

9. A spine stabilization rod assembly, comprising:
a one-piece rod having opposing end segments and a central segment extending between said opposing end segments, wherein the one-piece rod is substantially straight, wherein the opposing end segments of the rod are each intended to be and configured for being directly engaged by a rod fixation device and wherein a transition from the central segment to each one of said end segments defined a respective shoulder therebetween; and
a sleeve member coupled to the central segment of the one-piece rod, wherein the sleeve member is positioned over the central segment of the one-piece rod by relative displacement of the one-piece rod with respect to a central passage of the sleeve member such that the central segment passes through the central passage of the sleeve member and wherein only opposing end portions of the sleeve member are deformed after the sleeve member is positioned over the central segment for limiting unrestricted displacement of the sleeve member along a length of the central segment and such that portion of an inner surface of the central passage of the sleeve member between said deformed opposing end portions of the sleeve member is spaced away from an entire underlying portion of the central segment of the one-piece rod after the opposing end portions thereof are deformed.

10. The spine stabilization rod assembly of claim 9 wherein:
a first one of the end segments has a maximum outside diameter less than a minimum inside diameter of the central passage of the sleeve member prior to the opposing end portions thereof being deformed; and;
an overall length of the sleeve member is less than an overall length of the central segment.

11. The spine stabilization rod assembly of claim 9 wherein:
the first one of the end segments has a substantially round cross-sectional profile; and
a second one of said end segments has one of a substantially non-round cross-sectional profile and a substantially round cross-sectional profile having a maximum outside diameter that is substantially greater than a maximum outside diameter of the first end segment.

12. The spine stabilization rod assembly of claim 9, made by the process comprising:
sliding the sleeve member onto the rod such that the rod is within the central passage of the sleeve member;
positioning the sleeve member over the central segment; and
deforming only the opposing end portions of the sleeve member into contact with rod.

13. The spine stabilization rod assembly of claim 9 wherein:
an overall length of the sleeve member is less than an overall length of the central segment; and
an entire portion of the sleeve member is over the central segment.

14. A spine stabilization rod assembly, comprising:
a rod having a substantially round cross-sectional profile, a one-piece construction, and a substantially straight longitudinal axis, wherein the rod has a plurality of reduced diameter segments each between two adjacent nominal diameter segments thereof such that a shoulder is provided between the reduced diameter segment and each adjacent nominal diameter segment and wherein each one of the nominal diameter segments is intended to be and configured for being directly engaged by a rod fixation device; and
a plurality of sleeve members each positioned over a respective one of the reduced diameter segments of the rod, wherein each one of the sleeve members is positioned over the reduced diameter segment of the rod by relative displacement of the rod through a central passage of a respective one of the sleeve members, wherein only opposing end portions of each one of the sleeve members are deformed such that translation of a particular one of the sleeve members along the rod causes an end portion of the sleeve member to engage an adjacent shoulder of a respective one of the reduced diameter segments thereby limiting such translation and such that an entire portion of an inner surface of the central passage of each one of the sleeve members between said deformed opposing end portions thereof is spaced away from an entire underlying portion of a respective one of the reduced diameter segments of the rod after the opposing end portions thereof are deformed.

15. The spine stabilization rod assembly of claim 14, made by the process comprising:
- sliding the particular one of the sleeve members onto the rod such that the rod is within the central passage of the particular one of the sleeve members;
- positioning the particular one of the sleeve members over the respective one of the reduced diameter segments; and
- deforming only the opposing end portions of the particular one of the sleeve members into contact with rod.

16. The spine stabilization rod assembly of claim 14 wherein:
- an overall length of the particular one of the sleeve members is less than an overall length of the respective one of the reduced diameter segments.

17. The spine stabilization rod assembly of claim 14 wherein:
- an overall length of the particular one of the sleeve members is less than an overall length of the respective one of the reduced diameter segments;
- an entire portion of the particular one of the sleeve members is over the respective one of the reduced diameter segments; and
- only the opposing end portions of the particular one of the sleeve members are each deformed from an as-manufactured configuration such that the deformed portions of the particular one of the sleeve members are each engaged with the respective one of the reduced diameter segments.

* * * * *